US00PP32408P2

(12) United States Plant Patent
Kobayashi

(10) Patent No.: US PP32,408 P2
(45) Date of Patent: Oct. 27, 2020

(54) **NEW GUINEA *IMPATIENS* PLANT NAMED 'DONGISWEPICHE'**

(50) Latin Name: *Impatiens hawkeri*
Varietal Denomination: Dongiswepiche

(71) Applicant: DUMMEN GROUP B.V., De Lier (NL)

(72) Inventor: Ruth Kobayashi, Carlsbad, CA (US)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/602,037

(22) Filed: Jul. 25, 2019

(51) Int. Cl.
*A01H 5/02* (2018.01)
*A01H 6/16* (2018.01)

(52) U.S. Cl.
USPC ..... Plt./318.7
CPC ..... *A01H 6/165* (2018.05)

(58) Field of Classification Search
USPC ..... Plt./318.7
CPC ..... A01H 6/165
See application file for complete search history.

*Primary Examiner* — Anne Marie Grunberg
(74) *Attorney, Agent, or Firm* — C. A. Whealy

(57) ABSTRACT

A new and distinct cultivar of *Impatiens* plant named 'Dongiswepiche' characterized by its compact, upright to outwardly spreading and uniformly mounding plant habit; moderately vigorous growth habit; freely branching habit; glossy dark green-colored leaves; freely and early flowering habit; red-colored flowers with very light red-colored centers; and good garden performance.

2 Drawing Sheets

Botanical designation: *Impatiens hawkeri.*
Cultivar denomination: 'DONGISWEPICHE'.

BACKGROUND OF THE INVENTION

The present invention relates to a new and distinct cultivar of New Guinea *Impatiens* plant, botanically known as *Impatiens hawkeri* and hereinafter referred to by the name 'Dongiswepiche'.

The new *Impatiens* plant is a product of a planned breeding program conducted by the Inventor in Koka, Ethiopia and Encinitas, Calif. The objective of the breeding program is to create new early and freely flowering New Guinea *Impatiens* plants with attractive flowers and good garden performance.

The new *Impatiens* plant originated from a cross-pollination made by the Inventor in November, 2015 in Koka, Ethiopia of a proprietary selection of *Impatiens hawkeri* identified as code number NN-0009, not patented, as the female, or seed, parent with a proprietary selection of *Impatiens hawkeri* identified as code number NN13-001579-020, not patented, as the male, or pollen, parent. The new *Impatiens* plant was discovered and selected by the Inventor as a single flowering plant from within the progeny of the stated cross-pollination in a controlled greenhouse environment in Encinitas, Calif. in April, 2016.

Asexual reproduction of the new *Impatiens* plant by terminal vegetative cuttings in a controlled greenhouse environment in Encinitas, Calif. since June, 2016 has shown that the unique features of this new *Impatiens* plant are stable and reproduced true to type in successive generations.

SUMMARY OF THE INVENTION

Plants of the new *Impatiens* have not been observed under all possible combinations of environmental conditions and cultural practices. The phenotype may vary somewhat with variations in environmental conditions such as temperature, daylight and light intensity without, however, any variance in genotype.

The following traits have been repeatedly observed and are determined to be the unique characteristics of 'Dongiswepiche'. These characteristics in combination distinguish 'Dongiswepiche' as a new and distinct *Impatiens* plant:

1. Compact, upright to outwardly spreading and uniformly mounding plant habit.
2. Moderately vigorous growth habit.
3. Freely branching habit.
4. Glossy dark green-colored leaves.
5. Freely and early flowering habit.
6. Red-colored flowers with very light red-colored centers.
7. Good garden performance.

Plants of the new *Impatiens* can be compared to plants of the female parent selection. Plants of the new *Impatiens* differ primarily from plants of the female parent selection in the following characteristics:

1. Plants of the new *Impatiens* are not as compact as plants of the female parent selection.
2. Flowers of plants of the new *Impatiens* are red and very light red in color whereas flowers of plants of the female parent selection are pink and magenta in color.

Plants of the new *Impatiens* can be compared to plants of the male parent selection. Plants of the new *Impatiens* differ primarily from plants of the male parent selection in the following characteristics:

1. Plants of the new *Impatiens* have smaller flowers than plants of the male parent selection.
2. Flowers of plants of the new *Impatiens* are red and very light red in color whereas flowers of plants of the male parent selection are blush pink and light orange in color.

Plants of the new *Impatiens* can be compared to plants of *Impatiens hawkeri* 'Duepetrest', disclosed in U.S. Plant Pat.

No. 11,375. In side-by-side comparisons, plants of the new *Impatiens* differ primarily from plants of 'Duepetrest' in the following characteristics:

1. Plants of the new *Impatiens* are not as compact as plants of 'Duepetrest'.
2. The lower leaf surfaces of plants of the new *Impatiens* are green in color whereas the lower leaf surfaces of plants of 'Duepetrest' are dark red in color.
3. Plants of the new *Impatiens* have larger flowers than plants of 'Duepetrest'.
4. Flowers of plants of the new *Impatiens* are red and very light red in color whereas flowers of plants of 'Duepetrest' are soft red and light lavender bi-colored.

Plants of the new *Impatiens* can also be compared to plants of *Impatiens hawkeri* 'Dueptbus14', disclosed in U.S. Plant Pat. No. 26,780. In side-by-side comparisons, plants of the new *Impatiens* differ primarily from plants of 'Dueptbus14' in the following characteristics:

1. Plants of the new *Impatiens* are more compact than plants of 'Dueptbus14'.
2. The lower leaf surfaces of plants of the new *Impatiens* are green in color whereas the lower leaf surfaces of plants of 'Dueptbus14' are deep red in color.
3. Flowers of plants of the new *Impatiens* are red and very light red in color whereas flowers of plants of 'Dueptbus14' are bright red and red purple in color.

BRIEF DESCRIPTION OF THE PHOTOGRAPHS

The accompanying colored photographs illustrate the overall appearance of the new *Impatiens* plant showing the colors as true as it is reasonably possible to obtain in colored reproductions of this type. Colors in the photographs may differ slightly from the color values cited in the detailed botanical description which accurately describe the colors of the new *Impatiens* plant.

The photograph on the first sheet (sheet 1 of 2) is a side perspective view of a typical flowering plant of 'Dongiswepiche' grown in a container.

The photograph on the second sheet (sheet 2 of 2) is a close-up view of a typical flowering plant of 'Dongiswepiche'.

DETAILED BOTANICAL DESCRIPTION

The aforementioned photographs and following observations, measurements and values describe plants grown during the winter and spring in 20-cm containers in a polyethylene-covered greenhouse in Encinitas, Calif. and under cultural practices typical of commercial New Guinea *Impatiens* production. During the production of the plants, day temperatures averaged 26° C., night temperatures averaged 18° C. and light levels ranged from 4,000 to 5,000 lux. Plants were 19 weeks old when the photographs and description were taken. In the following description, color references are made to The Royal Horticultural Society Colour Chart, 2017 Edition, except where general terms of ordinary dictionary significance are used.

Botanical classification: *Impatiens hawkeri* 'Dongiswepiche'.

Parentage:

*Female, or seed, parent*.—Proprietary selection of *Impatiens hawkeri* identified as code number NN-0009, not patented.

*Male, or pollen, parent*.—Proprietary selection of *Impatiens hawkeri* identified as code number NN13-001579-020, not patented.

Propagation:

*Type*.—By terminal vegetative cuttings.

*Time to initiate roots, summer and winter*.—About five to seven days at day temperatures about 27° C. and night temperatures about 20° C.

*Time to produce a rooted young plant, summer and winter*.—About three weeks at day temperatures about 27° C. and night temperatures about 20° C.

*Root description*.—Fine, fibrous; typically white in color, actual color of the roots is dependent on substrate composition, water quality, fertilizers, substrate temperature and age of roots.

*Rooting habit*.—Freely branching; dense.

Plant description:

*Plant and growth habit*.—Compact, upright to outwardly spreading and uniformly mounding plant habit; broad inverted triangle in overall shape; freely branching habit; bushy and dense appearance; moderately vigorous growth habit and moderate growth rate.

*Plant height*.—About 21 cm.

*Plant diameter*.—About 42 cm.

Lateral branch description:

*Branching habit*.—Freely branching with about 12 to 15 primary lateral branches each with multiple secondary branches.

*Length*.—About 16 cm.

*Diameter*.—About 1.1 cm.

*Internode length*.—About 4 cm.

*Strength*.—Strong, flexible.

*Aspect*.—Initially upright to outwardly spreading, about 45° from vertical.

*Texture and luster*.—Smooth, glabrous; glossy.

*Color, developing*.—Close to 146A heavily tinged with close to 187A.

*Color, fully developed*.—Close to 146A; at the internodes, tinged with close to 187A.

Leaf description:

*Arrangement*.—Typically in whorls or opposite; simple.

*Length*.—About 8.5 cm.

*Width*.—About 3.25 cm.

*Shape*.—Obovate to elliptic.

*Apex*.—Long acuminate.

*Base*.—Attenuate.

*Margin*.—Serrate with ciliation.

*Texture and luster, upper surface*.—Smooth, glabrous; glossy.

*Texture and luster, lower surface*.—Smooth, glabrous; slightly glossy.

*Venation pattern*.—Pinnate; arcuate.

*Color*.—Developing leaves, upper surface: Close to 147A. Developing leaves, lower surface: Close to 147B. Fully expanded leaves, upper surface: Darker green than 147A; venation, close to 144A. Fully expanded leaves, lower surface: Close to 147B; venation, close to 144A to 144B tinged with close to 187B.

*Petiole length*.—About 3.5 cm.

*Petiole diameter*.—About 4 mm.

*Petiole texture and luster, upper surface*.—Smooth, glabrous; glossy.

*Petiole texture and luster, lower surface*.—Smooth, glabrous; somewhat glossy.

*Petiole color, upper and lower surfaces*.—Close to 144A to 144B slightly and variably tinged with close to 187B.

Flower description:

*Flower type and flowering habit*.—Single axillary flowers that are roughly rectangular in shape; freely flowering habit, typically about three to four opening and fully opened flowers per lateral branch; flowers are mostly flat and positioned above and beyond the foliar plane, flowers typically face mostly upright to outwardly.

*Flower longevity*.—Flowers typically last about four to seven days on the plant under greenhouse conditions; petals self-cleaning, gynoecium persistent.

*Fragrance*.—None detected.

*Natural flowering season*.—Year-round under greenhouse conditions; in the garden, flowering from spring until fall in California; early flowering habit, plants typically begin flowering about twelve weeks from unrooted cuttings.

*Flower buds*.—Length: About 1 cm. Diameter: About 6 mm. Shape: Ovoid. Texture and luster: Smooth, glabrous; somewhat glossy Color: Close to 144A.

*Flower diameter*.—About 5.4 cm by 4.8 cm.

*Flower depth*.—About 1 cm.

*Petals*.—Quantity and arrangement: Five per flower in a single whorl with one banner petal, two lateral petals and two lower petals. Length, banner petal: About 2.2 cm. Length, lateral petals: About 3.2 cm. Length, lower petals: About 2.6 cm. Width, banner petal: About 2.4 cm. Width, lateral petals: About 2.4 cm. Width, lower petals: About 2.4 cm. Shape, banner petals: Broadly cordate. Shape, lateral and lower petals: Cordate. Apex, all petals: Cordate. Base, all petals: Attenuate. Margin, all petals: Entire, slightly undulate. Texture and luster, all petals, upper and lower surfaces: Smooth, glabrous; somewhat glossy; iridescent. Color, all petals: When opening and fully opened, upper surface: Center, close to 52A; towards the margins, close to 52B; towards the base, close to 55D; venation, similar to lamina; very light red coloration becomes more dominant with development. When opening and fully opened, lower surface: Center, close to 55A; towards the margins, close to 55B; towards the base, close to 55D; venation, similar to lamina; color becoming closer to 55A with development.

*Sepals*.—Quantity and arrangement: Three in a single whorl; two laterals are opposite and the third modified into an elongated spur. Lateral sepal length: About 1.3 cm. Lateral sepal width: About 6 mm. Lateral sepal shape: Narrowly ovate. Lateral sepal apex: Long acuminate. Lateral sepal base: Truncate, fused. Lateral sepal margin: Entire. Lateral sepal texture and luster, upper and lower surfaces: Smooth, glabrous; somewhat glossy. Lateral sepal color, upper and lower surfaces: Close to 144C to 144D. Spur length: About 4 cm. Spur diameter: At flower, about 2 mm; at apex, less than 1 mm. Spur shape: Acicular, curved. Spur texture and luster: Smooth, glabrous; somewhat glossy. Spur color: Close to 144D slightly and variably tinged with close to 59B.

*Peduncles*.—Length: About 3.5 cm. Diameter: About 2 mm. Angle: About 30° to 45° from vertical. Strength: Strong; flexible. Texture and luster: Smooth, glabrous; moderately glossy. Color: Close to 144A to 144B.

*Reproductive organs*.—Stamens: Quantity: Five fused at anthers; filaments free. Filament length: About 4 mm. Filament color: Close to 158A. Anther length: About 4 mm. Anther shape: Oblong. Anther color: Close to N155B. Pollen amount: Moderate. Pollen color: Close to 158A. Pistils: Quantity per flower: One. Pistil length: About 5 mm. Stigma shape: Crested. Stigma color: Close to 144A. Style length: About 4 mm. Style color: Close to 144A. Ovary color: Close to 141A.

*Seeds and fruits*.—To date, seed and fruit production has not been observed on plants of the new *Impatiens*.

Pathogen & pest resistance: To date, plants of the new *Impatiens* have not been observed to be resistant to pathogens and pests common to *Impatiens* plants.

Garden performance: Plants of the new *Impatiens* have been observed to have good garden performance and tolerate temperatures ranging from about 5° C. to about 40° C.

It is claimed:

1. A new and distinct *Impatiens* plant named 'Dongiswepiche' as illustrated and described.

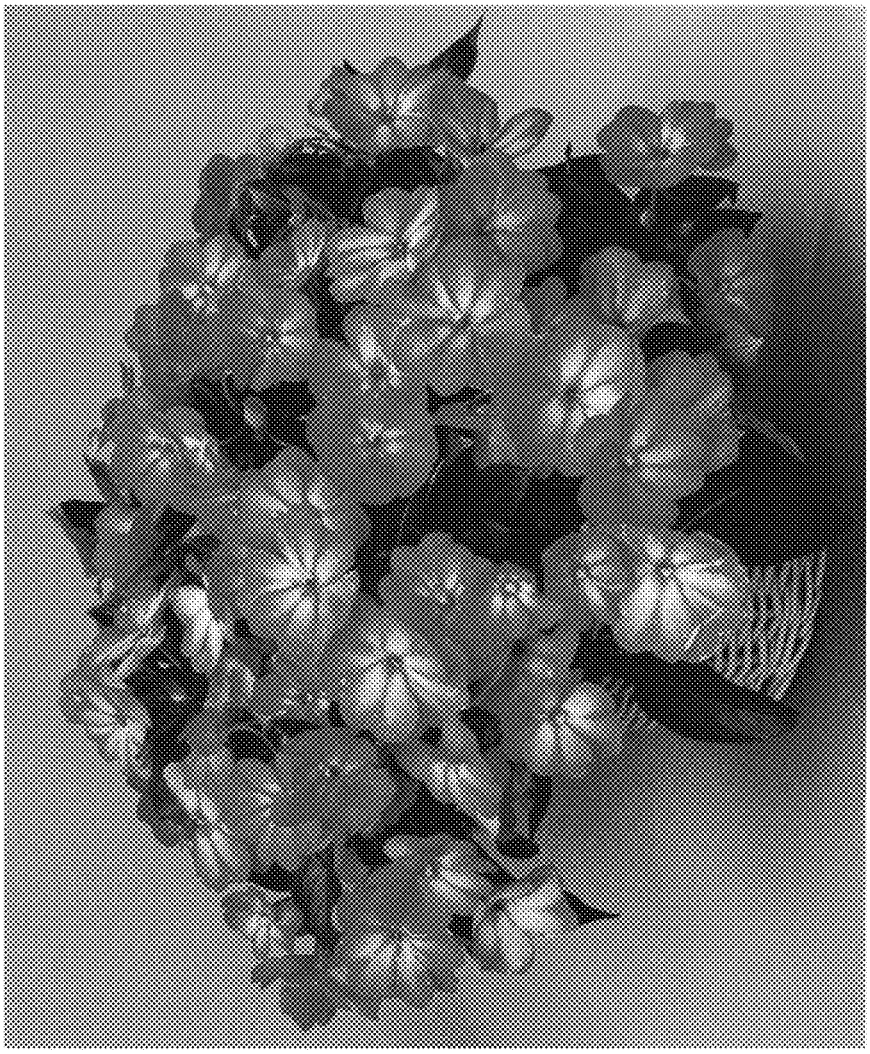

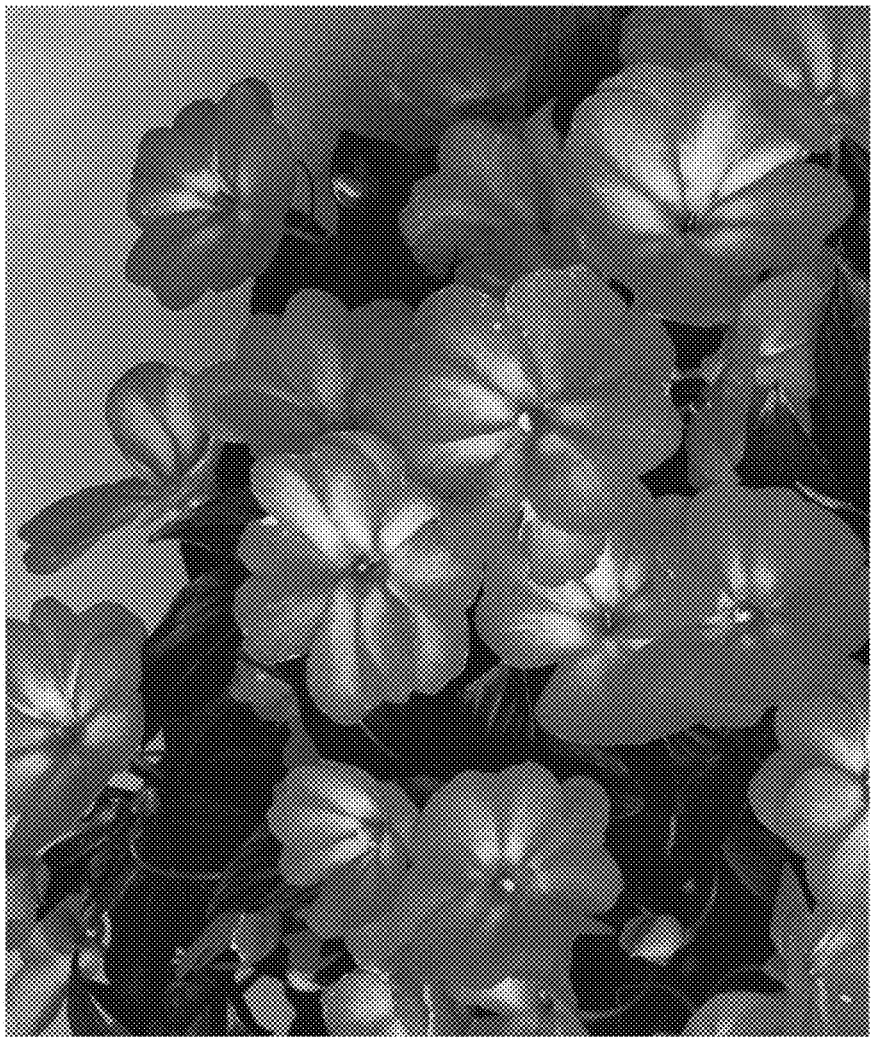

* * * * *